United States Patent
Beuthan et al.

(10) Patent No.: US 6,621,575 B1
(45) Date of Patent: Sep. 16, 2003

(54) METHOD AND DEVICE FOR ANALYZING MOLECULAR REACTION PRODUCTS IN BIOLOGICAL CELLS

(75) Inventors: Juergen Beuthan, Berlin (DE); Hans-Georg Eberle, Berlin (DE); Juergen Helfman, Kleinmachnow (DE); Gerhard Mueller, Berlin (DE)

(73) Assignee: Laser- und Medizin Technologie GmbH Berlin, Berlin (DE)

(*) Notice: Subject to any disclaimer, the term of this patent is extended or adjusted under 35 U.S.C. 154(b) by 0 days.

(21) Appl. No.: 10/181,785

(22) PCT Filed: Jan. 20, 2000

(86) PCT No.: PCT/EP00/00437

§ 371 (c)(1),
(2), (4) Date: Sep. 23, 2002

(87) PCT Pub. No.: WO01/53870

PCT Pub. Date: Jul. 26, 2001

(51) Int. Cl.$^7$ .................................................. G01J 3/30
(52) U.S. Cl. ...................................... 356/318; 250/306
(58) Field of Search .................. 356/318; 250/306, 250/307, 494.1

(56) References Cited

U.S. PATENT DOCUMENTS 4,659,429 A  4/1987  Isaacson

FOREIGN PATENT DOCUMENTS

| DE | 196 01 109 A1 | 7/1997 |
| DE | WO 98/58293 | * 12/1998 |
| DE | 198 58 490 A1 | 6/2000 |

* cited by examiner

Primary Examiner—Frank G. Font
Assistant Examiner—Layla Lauchman
(74) Attorney, Agent, or Firm—Hahn Loeser + Parks LLP; Stephen L. Grant

(57) ABSTRACT

A large number of cells can be evaluated in terms of their reaction state with molecular reactants under near-field optical conditions in a measuring and evaluation procedure of the invention. Light sources of different aperture diameters in the nano- or micro-range are disposed in a sample platform. The 2D-nano-light source array is embodied by a plurality of near-field light sources which are arranged in mutually juxtaposed relationship in raster form and are excited jointly or in succession. The carrier material used is a semiconductor material.

39 Claims, 3 Drawing Sheets

METHOD AND DEVICE FOR ANALYZING MOLECULAR REACTION PRODUCTS IN BIOLOGICAL CELLS

The invention concerns a method and apparatus for the analysis of molecular reaction products in relation to biological cells.

BACKGROUND OF THE ART

Structures below 0.2 μm can no longer be detected with a laser scan microscope. Light sources involving dimensions in the nanometer range are used for optical near-field microscopy. In that case the light sources are delimited by the apertures of tips of tapered optical fibers or micropipettes involving dimensions in the range of some ten nanometers. Conversely however the apertures can also be used to collect in light from the object. Two-dimensional registration of absorption or fluorescence of the nano-scale cell structures is achieved by serially scanning the object being investigated by the near-field probe. For that purpose the probe must be moved two-dimensionally (x-y-plane) and the near-field condition (probe-object spacing<50 nm) must be embodied at each x-y-position (image point).

In that way, it is in principle possible to investigate attachment mechanisms in relation to individual cells and cell membranes with near-field microscopy. When selecting a suitable wavelength for the lighting device particularly when the absorption of the sample molecules is known—it is possible to observe and/or measure attachment distribution on the surface of a cell membrane. With a modified arrangement and a suitably adapted method fluorescence-optical determination is also a possibility. In that case the emphasis lies on determining binding specificity.

Near-field microscopy in accordance with the state of the art however suffers from two serious limitations. On the one hand the attachment efficiency is to be determined only at one respective cell sequentially by way of series of tests which are tedious in terms of the time involved while on the other hand those investigations cannot be carried out, or can be carried out only in specific cases, in a humid nutrient medium. High-resolution (nano-scale) optical investigations of biological samples are possible at the present time with a sufficient degree of accuracy and reliability, only in the fixed or dry state. On the one hand because the needle probe influences the object to be investigated (spacing control by lateral force) and, in the case of cells in a nutrient solution, the approach for the purposes of observing the near-field condition is not guaranteed. On the other hand, in a procedure involving serial scanning by displacement of the probe (raster time for the entire image region: 30–300 s) a large part of the reaction kinetics on biological membranes is not detected (the attachment dynamics of antibodies on cell membrane proteins embraces the time range of ms to some seconds). High-resolution microscopy processes such as raster electron microscopy (REM) and transmission electron microscopy (TEM) in principle make it possible to measure off nano-scale structures. As their operating principle requires an evacuated environment and special sample preparation investigations in vivo or in vitro respectively are not possible. The samples are investigated generally in the dried or fixed state. Admittedly, on the basis of measurement of binding forces, atomic force microscopy permits investigation of the attachment of molecules to different cell constituents with sub-cellular resolution, but in this case also a severe influence on the cells and thus obscure results in investigations in a nutrient solution cannot be avoided. Clarification, which is important from scientific and technological points of view, of sub-cellular transport mechanisms—time-dynamic, locationally resolved and under physiological conditions—cannot be achieved with equipment available at the present time.

SUMMARY OF THE INVENTION

Therefore the object of the present invention is to provide an apparatus and a method with which a large number of cells can be evaluated in terms of their reaction state with molecular reactants under near-field optical conditions in a measuring and evaluation procedure. The object of the invention is in particular to determine the attachment efficiency of the molecular reactants in respect of attachment density in the cell partial areas in which the target proteins are disposed and in regard to attachment specificity which is given by virtue of the fact that the carrier or effective substance molecules bind only to special target proteins. In addition the object is characterised in that the determining operation must be implemented in a time-efficient manner on a large number of living cells—that is to say also in a nutrient medium—and that the determining operation is carried out on samples in the micro- and nano-scale range.

In accordance with the invention that object is attained in that a sample platform is provided, which is characterised in that fitted therein are light sources of different aperture diameters in the nano- and micro-range respectively. In accordance with the invention the geometrical arrangement thereof can be both unordered and also structurally ordered. The arrangement thereof relative to each other and the distribution functions in respect of number/aperture size groups are then to be presupposed to be known.

In accordance with the invention the two-dimensional nano-light sources array is embodied by a plurality of near-field light sources which are arranged in mutually juxtaposed relationship in a raster configuration and which are excited jointly or in succession. A semiconductor material, preferably silicon or GaAs, is used as the carrier material. The individual near-field light sources each have a respective hollow passage, wherein the individual hollow passages are used directly as nano-apertures for the exciting radiation or to produce secondary radiation (for example fluorescence or exciton radiation) are filled with a fluorescence- or exciton-active material. This nano-light source arrangement in accordance with the invention is covered by a 2–20 nm thick cover layer so that a large amount of sample of cells/cell membranes can be bound with a low degree of movement on the nano-source arrangement under a near-field condition for the time of the measurement procedure. It has surprisingly been found that biological objects (for example cells) can be fixed stably to the surface over a relatively long period of time by virtue of a biocompatible adhesion layer. In addition that layer guarantees that the near-field condition is constantly maintained. It is now possible without any problem to add a nutrient fluid which at the same time permits transport of the carrier and/or effective substance molecules to the membranes of the samples.

Upon registration of the overlap of the individual nano-light sources with the cell samples by counting off the bright points or measurement of the levels of light intensity it is surprisingly found that statistical evaluation of the distribution of intensity permits assessment of the lateral extent of the cells or active cell constituents. For that purpose the diameter and the distribution of the nano-light sources and the density in relation to surface area of the samples must be known. In that respect the aperture and the spacing of the nano-light sources are to be selected in a manner suited to the extent of the cells/cell nuclei belonging to a species.

The relative number of the nano-sources which overlap with objects depends on the known size and distribution density of the sources, and the size, shape and distribution density of the objects, in which respect shape has only a very slight influence. The overlap distribution can be determined by simple intensity measurement in a situation involving serial source excitation. The measured intensity distribution function (fluorescence or transmitted light) makes it possible to determine the object size, when the source size and distribution are known.

Attachment of the carrier and/or effective substance molecules to different proteins in the cell membrane, upon optical excitation of the resulting complexes by virtue of different binding energies, results in different absorption, excitation or secondary spectra (luminescence-, fluorescence-, Raman-scattered radiation etc). Wavelength-selective evaluation of the measured individual intensities (transmission or secondary radiation) thus, in addition to the effectiveness of attachment, also makes it possible to determine the selectivity thereof.

When different excitation spectra are involved the spectrum of the radiation from the nano-light sources must satisfy the demand for distinguishability of different attachment locations by virtue of the possibility of selective excitation (integral registration). When making use of the absorption or fluorescence differences the intensity is registered in spectrally resolved form.

The serial scanning which is very fast in terms of time (excitation) of the individual nano-light sources is effected in accordance with the invention selectively by a laser beam or by an electron beam. When laser beam excitation is used the nano-light sources can simply act as apertures or can emit fluorescence or exciton radiation by virtue of converter materials which are disposed in the apertures in accordance with the invention. The materials are so selected that their emission spectrum results in (selective) absorption or excitation of the sub-cellular structures being investigated, or causes intensive secondary radiation emission. In the case of serial electron beam excitation, an efficient cathodoluminescence- or exciton-active material is selectively introduced into the nano-aperture and excited for light emission from the side of the array, which is remote from the sample. In particular anthracene is suitable as an exciton-active material in the individual hollow passages, but it is also possible to use other exciton-active materials such as for example amorphous or porous silicon.

Optionally suitable materials in the nano-light sources cause them to be excited to emit other secondary radiation, for example luminescence or Raman radiation.

Detection is effected spatially integrally in the far field, in synchronised relationship with the serial excitation, effected in the raster mode, of the individual nano-light sources. The radiation can additionally be registered—if required—in wavelength-selective and/or time-resolved fashion. In order to determine the degree of overlap: cell assembly—nano-aperture matrix, in the simplest case intensity measurement which is related to the respective excitation location will suffice. The size of the cells or cell components can be ascertained by known methods of statistical microscopy from the measured individual intensities. If the dimensions of the cell or cell components which are of interest are known, it is possible to determine cell-specific distribution functions. Frequency-selective excitation and/or detection is provided for assessment of the attachment effectiveness and specificity.

BRIEF DESCRIPTION OF THE DRAWINGS

Better understanding of the present invention will be had when reference is made to the accompanying drawings, where identical parts are identified with identical reference numerals and wherein.

DETAILED DESCRIPTION OF A PREFERRED EMBODIMENT

Figure 1:
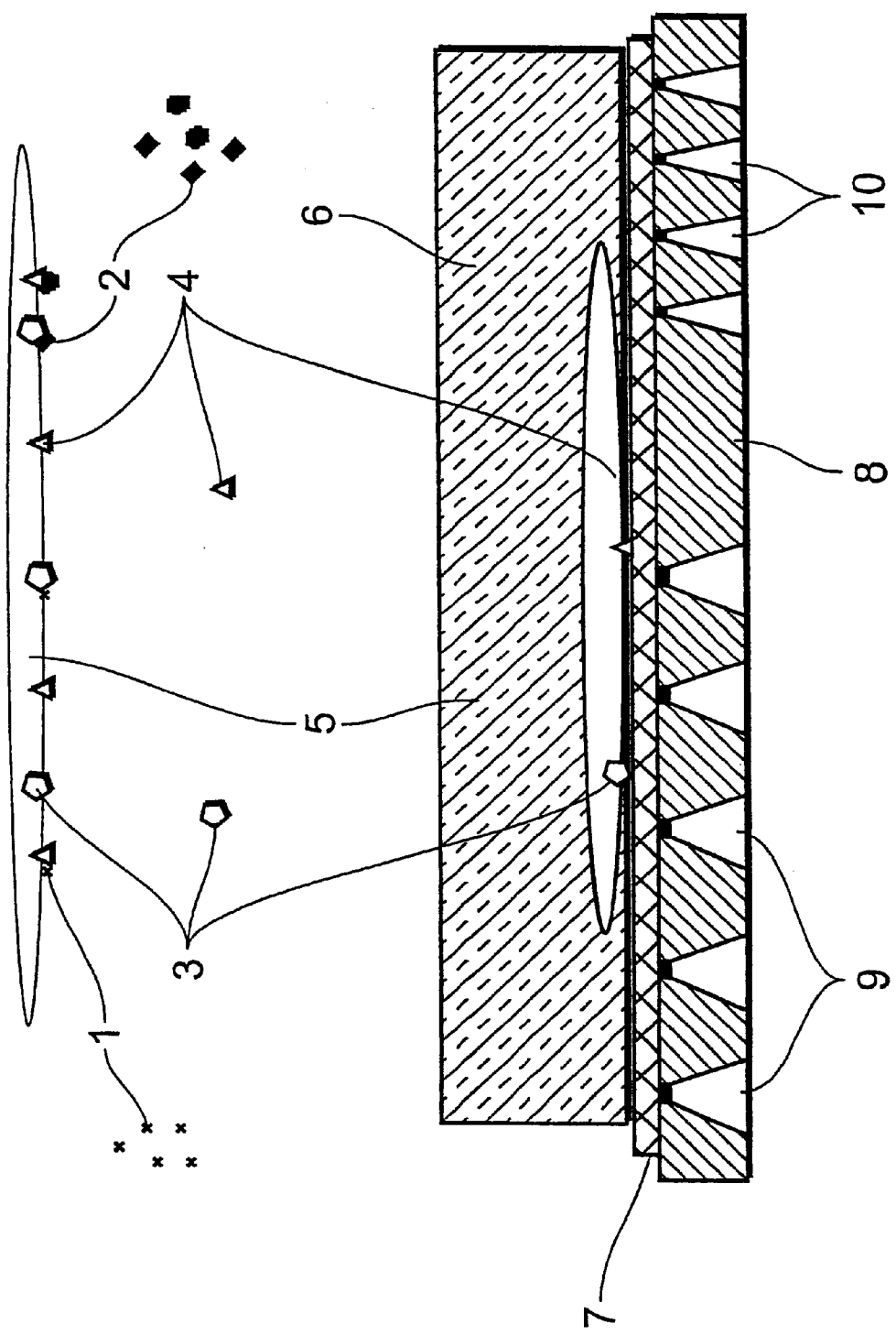
FIG. 1 is a side sectional view of the apparatus of the present invention.

In accordance with the invention a preferred embodiment in FIG. 1 shows that it is possible to determine the attachment efficiency in a 2-phase system of antibody groups 1 and 2 to especially distributed target protein groups 3 and 4 of the cell type. In FIG. 1 antibodies of groups 1 and 2 are put into the nutrient solution 6. The cell membranes lie on an adhesion layer 7 which itself is in turn disposed on the two-dimensional (2D) nano-source array or matrix 8. The nano-sources can have different apertures 9 and 10. The nano-source array 8 is formed by a two-dimensional arrangement of individual light sources or nano-light sources. The degree of covering of the individual nano-apertures is determined by measurement of the absorption or fluorescence intensity which is registered upon serial excitation and, in the case of wavelength-selective registration, permits a distinction to be drawn between the different attachment possibilities (1 or 2) to (3 or 4).

As a specific example, consideration can be given to the intermediate attachment of estrogens of type: beta-estradiol on mammary carcinoma cells prior to transport through the cell membrane. The cells have receptors for estrogens. Attachment to those receptors results in a shift of the fluorescence wavelength, which applies in regard to unbound estrogens, of 569 nm (50 mmolar in ethanol, excitation at 488 nm). When a known number of mammary carcinoma cells are disposed in the nutrient solution, intermediate attachment to the cell membrane will occur upon the addition of estrogens of known concentration. Attachment specificity to the receptor being considered can be determined by comparison of the levels of intensity registered at the shifted wavelength, relative to the total intensity.

Figure 2:
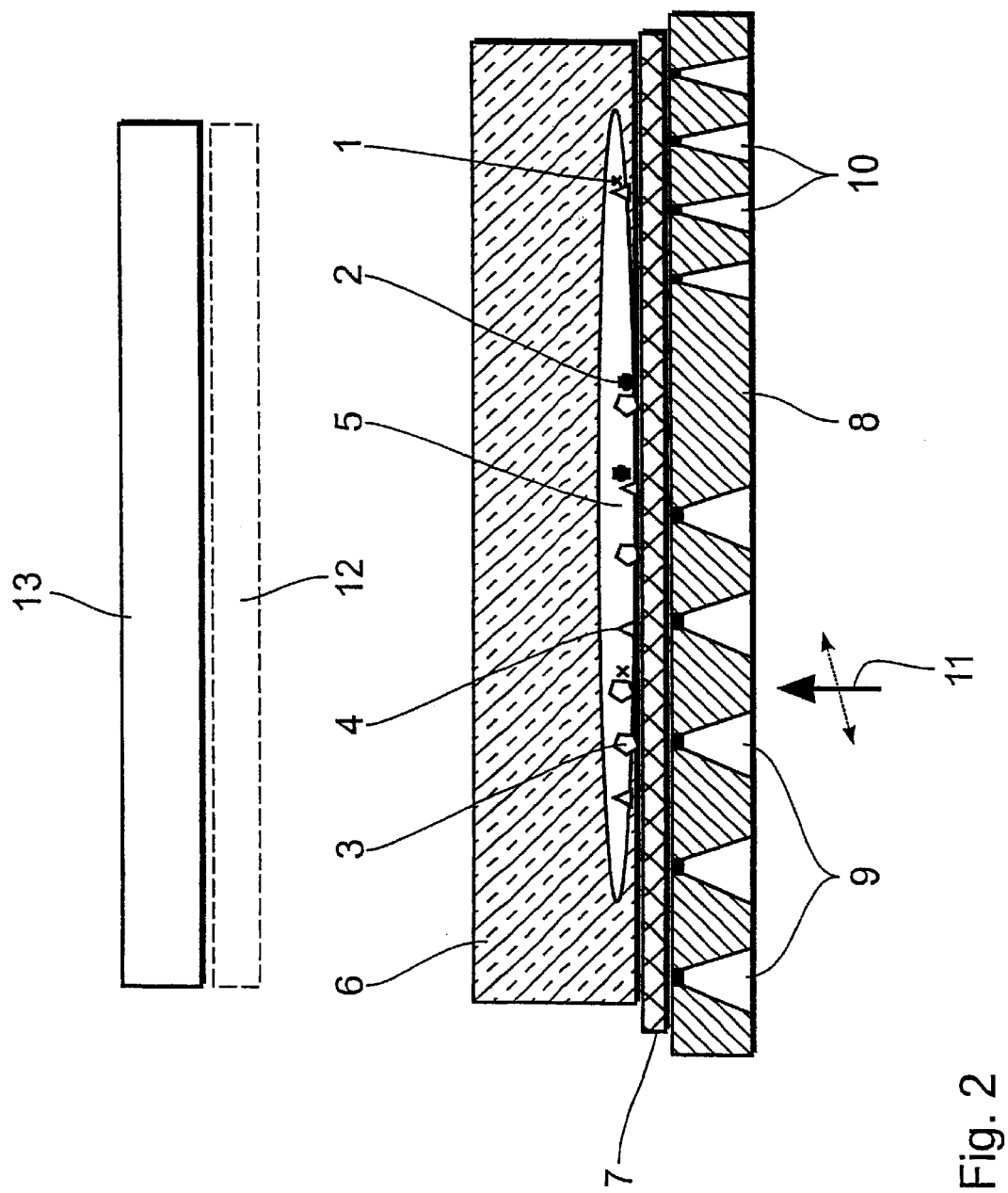
FIG. 2 is a side sectional view of the present invention apparatus, showing the complete measuring arrangement of the exciting electron or laser beam.

FIG. 2 shows the complete measuring arrangement with the exciting electron or laser beam 11 which is guided in a raster mode over the nano-source matrix 8. In this case excitation is effected by observing the near-field condition in such a way that the resolution is better than 200 nm. The radiation transmitted through the sample or the fluorescence radiation issuing therefrom is registered with a large-area detector 13 in the far field. Depending on the respective task involved according to the invention the radiation is selectively spectrally broken down by a monochromator 12 and wavelength-selective detection is implemented.

Figure 3:
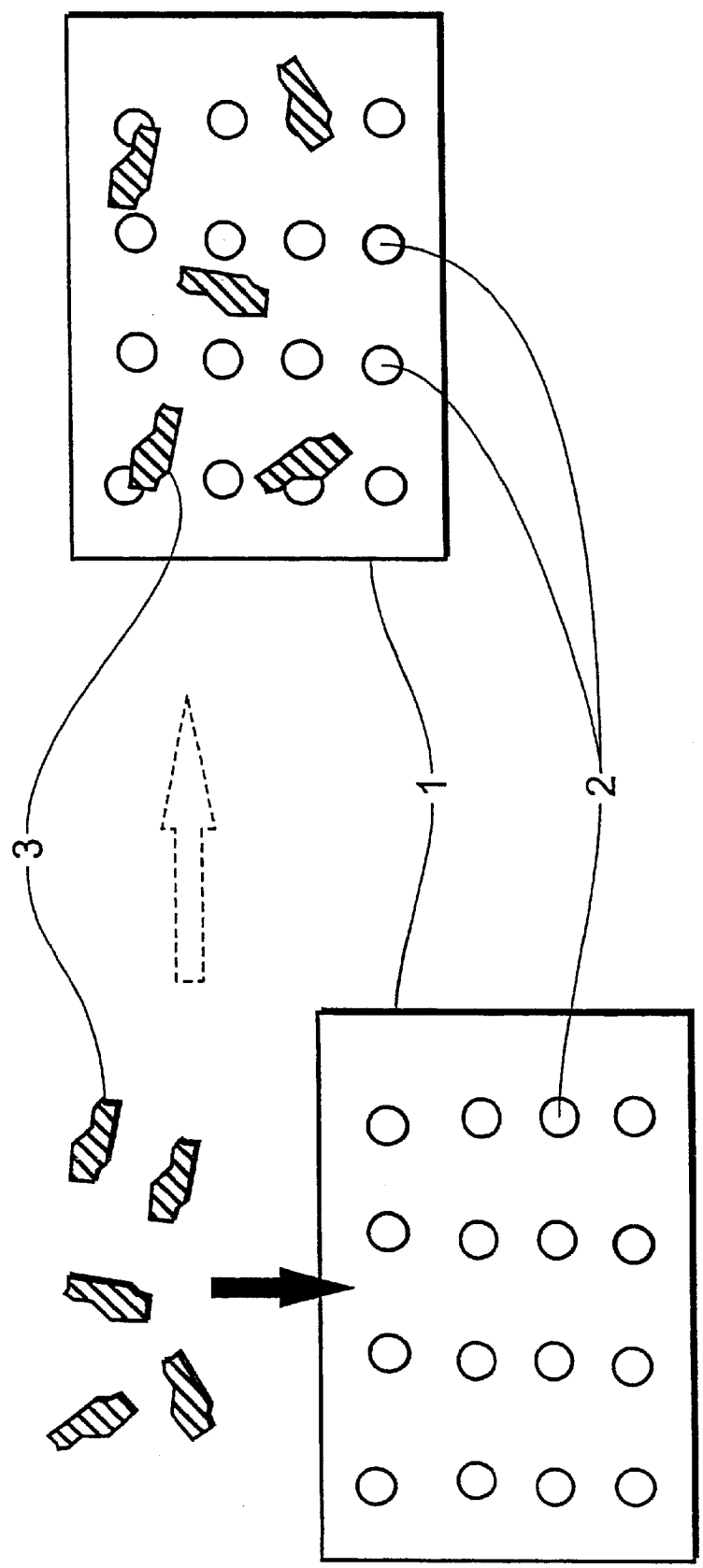
FIG. 3 is a top plan view of the apparatus, showing the possible degrees of overlap of an arrangement of nano-apertures by cells or cell components.

FIG. 3 shows the possible degrees of overlap of an arrangement 1 of nano-apertures (nano-light sources) 2 by cells or cell components 3. Depending on the respective degree of covering of the nano-light sources the result is a differing level of transmitted or fluorescence intensity upon serial excitation of the individual nano-light sources.

In order to be able to determine the size of molecules or cell components with statistical microscopy methods, the distribution and the diameters of the apertures of the nano-light source matrix as well as the lateral concentration of the objects being investigated must be known. Arrays involving different aperture diameters and spacings are to be used for investigating nano-objects of markedly different sizes. By wavelength-selective excitation and/or wavelength-selective detection it is possible to distinguish between two (or more) molecule types or molecule complexes occurring due to attachment of molecules (for example effective substance molecules or antibodies). For that purpose the intensity of the radiation which is emitted upon time-sequential excitation of the individual nano-light sources and which is influenced by the object to be investigated or the fluorescence radiation produced in that situation must be wavelength-selectively registered.

To sum up the invention concerns an apparatus and a method with which a large number of cells can be evaluated in terms of their reaction state with molecular reactants under near-field optical conditions in a measuring and evaluation procedure.

A sample platform is characterised in that light sources of different aperture diameters in the nano- or micro-range are disposed therein. The 2D-nano-light source array is embodied by a plurality of near-field light sources which are arranged in mutually juxtaposed relationship in raster form and are excited jointly or in succession. The carrier material used is a semiconductor material.

What is claimed is:

1. A two-dimensional nano-light source carrier for the analysis of biological objects with near-field optical methods, comprising
   (a) a plurality of individual light sources, and
   (b) a cover layer which is applied to the carrier on an object side thereof and which protects the carrier against possible actions due to the objects to be investigated;
   wherein the individual light sources are arranged in hollow passages of the carrier;
   wherein the individual light sources have a diameter in the nano- to micrometer range, and
   wherein the individual light sources are filled with an excitation-active converter material.

2. The two-dimensional nano-light source carrier as set forth in claim 1 wherein the cover layer is between 2 and 20 nm thick.

3. The two-dimensional nano-light source carrier of claim 2, wherein an adhesion layer is applied to the cover layer and holds the biological object to be measured in a nutrient solution in a manner which does not influence the metabolism and transport mechanisms of the biological nano-preparations.

4. The two-dimensional nano-light source carrier as set forth in claim 3 characterised in that the adhesion layer comprises lipids.

5. The two-dimensional nano-light source carrier as set forth in claim 3 characterised in that the adhesion layer comprises cellulose derivatives.

6. The two-dimensional nano-light source carrier of claim 3, wherein the excitation-active converter material comprises amorphous silicon.

7. The two-dimensional nano-light source carrier of claim 3, wherein the carrier comprises silicon.

8. The two-dimensional nano-light source carrier of claim 3, wherein the hollow passages form a two-dimensional matrix of nano-apertures.

9. An apparatus for the analysis of biological objects with near-field optical methods, comprising:
   (a) a primary excitation source which provides an excitation radiation in the form of a laser or electron beam, and
   (b) a 2D-nano-light source carrier comprising
      a plurality of individual light sources which are arranged in hollow passages of the carrier, are of a diameter in the nano- to micro-range and are filled with an excitation-active converter material, and
      a cover layer which is applied to the carrier on the object side and which protects the carrier against possible actions due to the objects to be investigated.

10. The apparatus as set forth in claim 9 characterised in that the primary excitation source further comprises a vacuum chamber arranged on a side of the carrier remote from the biological objects, for producing the electron beam, the chamber being separated by an electron window from the biological objects which are in normal atmosphere.

11. The apparatus of claim 10, wherein the electron window comprises beryllium.

12. The apparatus of claim 10, further comprising a detector for spatially integral detection of a secondary radiation in the region of the biological objects.

13. The apparatus of claim 12, comprising a monochromator is connected upstream of the detector.

14. A method of analysing biological objects with near-field optical methods, comprising the following steps in an apparatus:
   (a) producing an excitation radiation in the form of a laser or electron beam by a primary excitation source,
   (b) deflecting the excitation radiation onto a two-dimensional nano-light source carrier comprising a plurality of individual light sources which are arranged in hollow passages of the carrier, are of a diameter in the nano- to micro-range and are filled with an excitation-active converter material, and a cover layer which is applied to the carrier on an object side thereof and which protects the carrier against possible actions due to the objects to be investigated,
   (c) exciting the excitation-active converter material by the excitation radiation to emit a secondary radiation which impinges on the biological objects to be investigated, and
   (d) detecting with a detector spatially integrally the secondary radiation in the region of the biological objects.

15. The method as set forth in claim 14, wherein a laser with a wavelength range of between 0.150 $\mu$m and 11.0 $\mu$m is used as the excitation source.

16. The method as set forth in claim 14, wherein an electron beam with an energy in the range of between 0.01 eV and 10 keV is used as the excitation source.

17. The method of claim 15, wherein detection is effected in time-selective and/or wavelength-selective manner.

18. The method as set forth in claim 17, wherein a plurality of different cell types or cell components are investigated by spectrally selective registration and determination of the statistical distribution functions.

19. The method of claim 18, wherein the individual light sources are subjected to raster scanning by the laser beam or electron beam.

20. The method of claim 19, wherein an excitation wavelength is used that results in an intensive secondary radiation only in relation to a target complex of the biological objects while using selective excitation of the target complex.

21. The method as set forth in claim 20, wherein wavelength-selective detection of the secondary radiation emitted by the excited cell complexes is effected.

22. The method of claim 21, wherein the method determines the effectiveness of attachment of effective substance molecules and/or carrier molecules to cell components of known statistical distribution.

23. The method of claim 21, wherein the method determines the selectivity of the attachment of effective substance molecules and/or carrier molecules to predetermined target molecule groups of known statistical distribution.

24. The two-dimensional nano-light source carrier of claim 1, wherein an adhesion layer is applied to the cover layer and holds the biological object to be measured in a nutrient solution in a manner which does not influence the metabolism and transport mechanisms of the biological nano-preparations.

25. The two-dimensional nano-light source carrier of claim 3, wherein the excitation-active converter material comprises porous silicon.

26. The two-dimensional nano-light source carrier of claim 3, wherein the excitation-active converter material comprises anthracene.

27. The two-dimensional nano-light source carrier of claim 1, wherein the excitation-active converter material comprises amorphous silicon.

28. The two-dimensional nano-light source carrier of claim 1, wherein the excitation-active converter material comprises porous silicon.

29. The two-dimensional nano-light source carrier of claim 1, wherein the excitation-active converter material comprises anthracene.

30. The two-dimensional nano-light source carrier of claim 3, wherein the carrier comprises gallium arsenide.

31. The two-dimensional nano-light source carrier of claim 1, wherein the carrier comprises silicon.

32. The two-dimensional nano-light source carrier of claim 1, wherein the carrier comprises gallium arsenide.

33. The two-dimensional nano-light source carrier of claim 1, wherein the hollow passages form a two-dimensional matrix of nano-apertures.

34. The apparatus of claim 10, wherein the electron window comprises Kapton.

35. The method of claim 14, wherein detection is effected in time-selective and/or wavelength-selective manner.

36. The method of claim 14, wherein the individual light sources are subjected to raster scanning by the laser beam or electron beam.

37. The method of claim 14, wherein an excitation wavelength is used that results in an intensive secondary radiation only in relation to a target complex of the biological objects while using selective excitation of the target complex.

38. The method of claim 19, wherein the target complex is a target molecule with effective substance molecule and/or carrier molecule attached thereto.

39. The method of claim 37, wherein the target complex is a target molecule with effective substance molecule and/or carrier molecule attached thereto.

\* \* \* \* \*